United States Patent [19]

Drent

[11] Patent Number: 4,730,080

[45] Date of Patent: Mar. 8, 1988

[54] PROCESS FOR THE PREPARATION OF DIESTERS OF ALKANEDIOIC ACIDS

[75] Inventor: Eit Drent, Amsterdam, Netherlands

[73] Assignee: Shell Oil Company, Houston, Tex.

[21] Appl. No.: 879,669

[22] Filed: Jun. 27, 1986

[30] Foreign Application Priority Data

Aug. 29, 1985 [GB] United Kingdom ............... 8521492

[51] Int. Cl.$^4$ .............................................. C07C 67/38
[52] U.S. Cl. ..................................... 560/204; 502/102; 502/162; 502/165; 502/166; 502/171; 502/213; 502/225; 502/229; 502/313; 560/193; 562/590; 562/597
[58] Field of Search ............. 560/204, 19 B; 562/590; 502/102, 162, 165, 166, 171, 213, 225, , 229, 313

[56] References Cited

U.S. PATENT DOCUMENTS

| 4,076,949 | 2/1978 | Zehner | 560/204 |
| 4,585,891 | 4/1986 | Morris | 560/204 |
| 4,642,374 | 2/1987 | Lucy et al. | 560/204 |

OTHER PUBLICATIONS

Journal of Molecular Analysis 14 (1982), 113–120.

*Primary Examiner*—Werren B. Lone
*Assistant Examiner*—Vera C. Clarke

[57] ABSTRACT

Preparation of diesters of alkanedioic acids by reacting a dihydrocarbyl peroxide with carbon monoxide and optionally with an alpha-ethylenically unsaturated compound in the presence of a solvent, a Group VIII noble metal or a compound thereof and of a cupric salt.

10 Claims, No Drawings

PROCESS FOR THE PREPARATION OF DIESTERS OF ALKANEDIOIC ACIDS

FIELD OF THE INVENTION

This invention relates to a process for the preparation of diesters of alkanedioic acids.

BACKGROUND OF THE INVENTION

It is known from Journal of Molecular Catalysis 14 (1982) 113-120 that an alpha-olefin, tert-butyl hydroperoxide and carbon monoxide react in the presence of palladium-phosphine mixtures with formation of ketones, monoalkanoic acids and esters thereof, without formation of diesters of alkanedioic acids.

It is an object of the present invention to prepare diesters of alkanedioic acids in a high yield.

SUMMARY OF THE INVENTION

This invention relates to a process for the preparation of diesters of alkanedioic acids, which process comprises reacting a dihydrocarbyl peroxide with carbon monoxide and optionally with an alpha-ethylenically unsaturated compound in the presence of a solvent and of a catalytic system formed by combining (a) a noble metal or a compound thereof of Group VIII of the Periodic Table of the Elements and (b) a cupric salt.

DESCRIPTION OF THE PREFERRED EMBODIMENTS

The noble metals which may be used are platinum, palladium, rhodium, osmium, iridium and ruthenium. These metals may be used in finely divided form, not supported on a carrier, or supported on a carrier, for example on activated carbon. Compounds of each of these noble metals may be used. It is also possible to use mixtures of these noble metals and/or mixtures of compounds of these noble metals. Very good results have been obtained with palladium and with compounds of palladium. Examples of suitable compounds are salts, such as halides (fluorides, chlorides, bromides, iodides), nitrates, sulfates and carboxylates, preferably alkanoates derived from alkanoic acids having not more than 12 carbon atoms per molecule. Very good results have been obtained with palladium(II) chloride. Further examples of suitable palladium compounds are palladium complexes such as bis(2,4-pentanedionato)palladium, bis(picolinato)palladium, tetrakis(triphenylphosphine)palladium, tetrakisacetonitrile palladium tetrafluoroborate, bis(tri-o-tolylphosphine)palladium acetate, bis(triphenylphosphine)palladium sulfate, palladium olefin complexes, for instance di-$\mu$-chlorodichlorobis(ethylene)dipalladium ($[Pd.C_2H_4.Cl_2]_2$), di-$\mu$-chlorodichlorobis(propylene)dipalladium ($[Pd.C_3H_6.Cl_2]_2$) and palladium hydride complexes.

Cupric salts are surprisingly effective in the formation of diesters of alkanedioic acids. When the process according to the present invention is modified by replacing cupric salts with, for example, a vanadium salt, almost no reaction is found. Examples of suitable cupric salts are cupric chloride, cupric nitrate, cupric sulfate and cupric carboxylates, preferably having not more than 12 carbon atoms per molecule. Very good results have been obtained with cupric chloride.

The process according to the present invention may be carried out using a molar ratio of noble metal or compound thereof to dihydrocarbyl peroxide which is not critical and may vary within wide limits. This molar ratio is suitably in the range of from $10^{-2}$ to $10^{-5}$.

The process according to the present invention may be carried out using a molar ratio cupric salt to noble metal or compound thereof which is not critical and may vary within wide limits. This molar ratio is suitably in the range of from 0.5 to 500 and preferably of from 1 to 100.

The process according to the invention results, when an alpha-ethylenically unsaturated compound is a reactant, in the formation of esters of succinic acid or derivative thereof and may be represented by means of the general equation(1):

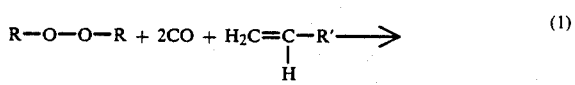

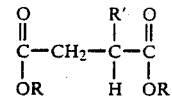

wherein each R represents a substituted or unsubstituted hydrocarbyl group which may be the same or different and R' represents a substituted or unsubstituted hydrocarbyl group.

The process according to the invention results, when an alpha-ethylenically unsaturated compound is not a reactant, in the formation of esters of oxalic acid and may be represented by means of the general equation(2):

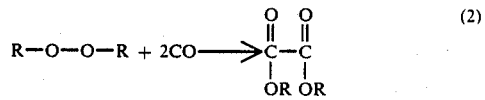

wherein each R has the same meaning as in the general equation(1).

The hydrocarbyl groups R in the general equations (1) and (2) and the hydrocarbyl group R' in the general equation (1) may be an alkyl, cycloalkyl, aryl, alkaryl or aralkyl group, each thereof suitably having up to 20 carbon atoms. The hydrocarbyl group R is preferably an alkyl group and more preferably an alkyl group having from 1 to 6 carbon atoms. Very good results have been obtained with di-tert-butyl peroxide. Other examples of suitable peroxides are di-n-butyl peroxide, di-sec-butyl peroxide, di-isopropyl peroxide and dicumyl peroxide.

The alpha-ethylenically unsaturated compound is preferably an alpha-alkene. Very good results have been obtained with alpha-alkenes having up to 10 carbon atoms per molecule, particularly with ethene and propene. Other examples of suitable alpha-alkenes are 1-butene, 1-pentene, 1-hexene, 1-heptene, 1-octene, 1-nonene and 1-decene.

The alpha-ethylenically unsaturated compound may carry substituents which are inert under the prevailing reaction conditions, such as nitro groups, chlorine atoms or alkoxy groups, suitably having not more than 10 carbon atoms.

If it is desired to enhance the formation of esters of oxalic acid, a trihydrocarbylphosphine oxide may also be combined with the catalytic system. The hydrocarbyl groups therein may be alkyl, cycloalkyl or aryl groups and may carry substituents, for example nitro, cyano or methoxy groups. Very good results have been obtained with triarylphosphine oxides, particularly with triphenylphosphine oxide. Suitably, a molar ratio of trihydrocarbylphosphine oxide to noble metal or compound thereof in the range of from 0.5 to 100 is used.

The process according to the invention is carried out in the presence of a solvent for the catalytic system, for example an alkanol, such as those having in the range from 1 to 8 carbon atoms per molecule; examples of such alkanols are methanol, ethanol, propanol, 2-propanol, butanol, 2-butanol, tert-butyl alcohol and pentanol. Other examples of suitable solvents are ethers, such as methyl ethyl ether, diethyl ether, dipropyl ether, tetrahydrofuran, dimethyl ether of diethylene glycol (also referred to as "diglyme"), methyl tert-butyl ether and 1,4-dioxane; halogenated hydrocarbons such as chloroform, chlorobenzene and perfluoroalkanes; ketones such as acetone, diethyl ketone and methyl isobutyl ketone; esters, such as methyl formate, ethyl formate, propyl formate, methyl acetate, ethyl acetate, propyl acetate and methyl or ethyl esters of adipic acid, succinic acid, maleic acid, fumaric acid, propionic acid, oxalic acid and benzoic acid. The diesters formed by the process according to the invention may be used as a solvent, for example di-tert-butyl oxalate or diethyl succinate. Other examples of suitable solvents are dimethyl sulfone, methyl butyl sulfone and tetrahydrothiophene 1,1-dioxide (also referred to as "sulfolane"); sulfoxides such as diemthyl sulfoxide and diethyl sulfoxide; aromatic hydrocarbons such as benzene, toluene and the three xylenes; cycloalkanes such as cyclohexane; nitrobenzene.

The process according to the present invention can be carried out in wide ranges of temperature and pressure, preferably in the range of from 20° C. to 200° C., more preferably from 50° C. to 125° C., and at a pressure preferably in the range of from 5 to 200 bar, more preferably from 10 to 100 bar.

The process according to the invention can be carried out batchwise, semi-continuously or continuously. The reaction time may vary in relation to the temperature used and is usually between 0.5 and 20 hours.

The following examples are intended to further illustrate the invention and are not to be construed as limiting the invention. All experiments were carried out in a 300 ml autoclave made of Hastelloy C ("Hastelloy" is a trade name) provided with a magnetically driven stirrer. In all experiments the autoclave was charged with tert-butyl alcohol (40 ml), a peroxide, other reactants and the catalytic system, as detailed hereinafter, heated to 100° C. (except where otherwise stated) and kept at this temperature for 4 hours. Then the conversion of the peroxide and the selectivities to esters of alkanedioic acids were determined. The selectivity to a certain compound, expressed in a percentage, is defined herein as 100 a/b, in which "a" is the amount of peroxide that has been converted into that certain compound and "b" is the total amount of peroxide that has been converted

EXAMPLE 1

The autoclave was charged with di-tert-butyl peroxide (5 ml), carbon monoxide (20 bar), ethylene (20 bar), palladium(II) chloride (0.1 mmol) and cupric chloride (2 mmol). The conversion of the peroxide was 95% and the selectivity to di-tert-butyl succinate was 55%, and to tert-butyl 3-tert-butoxypropionate 30%. Formation of oxalate had not been observed.

EXAMPLE 2

An experiment was run in the same manner as Example 1, except that 1 mmol instead of 2 mmol of cupric chloride was used. The conversion of the peroxide was 60% and the selectivities to di-tert-butyl succinate and di-tert-butyl oxalate were 80% and 5%, respectively. Only traces of tert-butyl 3-tert-butoxy-propionate were found.

EXAMPLE 3

The autoclave was charged with di-tert-butyl peroxide (5 ml), carbon monoxide (20 bar), propene (8 bar), palladium(II) chloride (0.1 mmol) and cupric chloride (0.5 mmol). The conversion of peroxide was 50% and the selectivities to di-tert-butyl 2-methylsuccinate and di-tert-butyl oxalate were 30% and 50%, respectively.

EXAMPLE 4

An experiment was run in the same manner as Example 3, except that no propene was present, the partial pressure of carbon monoxide was 40 bar instead of 20 bar and the temperature was kept at 110° C. for an additional hour, the total reaction time being 5 hours. The conversion of peroxide was 20% and the selectivity to di-tert-butyl oxalate was 20%.

EXAMPLE 5

An experiment was run in the same manner as Example 4, except that triphenylphosphine oxide (3 mmol) was also present and that the temperature was not kept at 110° C. for an hour. The conversion of peroxide was 60% and the selectivity to di-tert-butyl oxalate was 80%.

EXAMPLE 6

An experiment was run in the same manner as Example 3, except that 1 mmol of triphenylphosphine oxide was also present. The conversion of peroxide was 45% and the selectivities to di-tert-butyl 2-methylsuccinate and di-tert-butyl oxalate were 15% and 70%, respectively.

EXAMPLE 7

The autoclave was charged with di-tert-butyl peroxide (5 ml), carbon monoxide (40 bar), 1 g of palladium on active carbon (0.5% wt Pd on carbon) and cupric chloride (0.5 mmol). The conversion of peroxide was 50% and the selectivity to di-tert-butyl oxalate was 95%.

COMPARATIVE EXPERIMENT A

An experiment was run in the same manner as Example 2, except that the 5 ml of di-tert-butyl peroxide was replaced with 5 ml of tert-butyl hydroperoxide; the temperature rapidly increased to 110° C. from 50° C. at the start. Formation of succinates and oxalates has not been observed.

COMPARATIVE EXPERIMENT B

An experiment was run in the same manner as Example 7, except that no cupric chloride was present. Formation of oxalates has not been observed.

COMPARATIVE EXPERIMENT C

The autoclave was charged with di-tert-butyl peroxide (5 ml), carbon monoxide (20 bar), ethylene (30 bar), palladium(II) chloride (0.1 mmol) and vanadium(III)

chloride (2 mmol). The conversion of peroxide was less than 10% and only traces of succinate and oxalate had been found.

I claim as my invention:

1. A process for the preparation of diesters of alkanedioc acids, which process comprises reacting at a temperature in the range of from 20° C. to 200° C. and a pressure in the range of 5 to 200 bar a dihydrocarbyl peroxide with carbon monoxide and with an alpha-alkene having 2 to 10 carbon atoms per molecule in the presence of a solvent and a catalyst system formed by combining (a) a noble metal or a compound thereof of Group VIII of the Periodic Table of the Elements and (b) a cupric salt.

2. The process of claim 1 wherein a palladium compound is used.

3. The process of claim 2 wherein the palladium compound is a salt of divalent palladium.

4. The process of claim 1 wherein a molar ratio of cupric salt to noble metal or compound thereof in the range of from 1 to 100 is used.

5. The process of claim 1 wherein the dihydrocarbyl peroxide is a diakyl peroxide.

6. The process of claim 5 wherein the diakyl peroxide is di-tert-butyl peroxide.

7. The process of claim 1 wherein the alkene is ethene.

8. The process of claim 1 wherein the alkene is propene.

9. The process of claim 1 wherein a trihydrocarbylphosphine oxide is also combined with the catalyst system.

10. The process of claim 9 wherein the trihydrocarbylphosphine oxide is triphenylphosphine oxide.

* * * * *